United States Patent [19]

Kourbatov et al.

[11] Patent Number: 5,488,192
[45] Date of Patent: Jan. 30, 1996

[54] METHOD FOR INHIBITING THE POLYMERIZATION OF STYRENE

[75] Inventors: Vladimir A. Kourbatov, Moscow; Nataljya P. Boreyko; Valerii P. Zouev, both of Nischnekamsk; Alexandr G. Liakumovich, Kazan, all of Russian Federation

[73] Assignee: Kourbatov, Moscow, Russian Federation

[21] Appl. No.: 238,670

[22] Filed: May 5, 1994

[51] Int. Cl.⁶ ........................................ C07C 5/333
[52] U.S. Cl. ................... 585/435; 585/2; 585/3; 585/4; 585/5; 585/440
[58] Field of Search ........................... 585/2, 3, 4, 5, 585/435, 440

[56] References Cited

FOREIGN PATENT DOCUMENTS

| 257496 | 11/1968 | U.S.S.R. |
| 441263 | 5/1972 | U.S.S.R. |
| 819078 | 7/1978 | U.S.S.R. |

*Primary Examiner*—Ponnathapura Achutamurthy
*Attorney, Agent, or Firm*—Jacobson, Price, Holman & Stern

[57] ABSTRACT

In the production of styrene, spontaneous polymerization of styrene monomer causes reduced efficiency and as such it is desirable to prevent the formation of polymer by the addition of inhibitors. A known inhibiting composition is 3,5-di-tert-butyl-4-hydroxy-N,N-dimethylbenzyl amine and carboxylic acid, or an anhydride of said carboxylic acid which is added to a styrene-containing mixture. However large quantities are required and often portions of the inhibiting composition are not utilized resulting in nonproductive loss. The efficiency of the specific inhibitor can be improved by supplying air simultaneously with the inhibiting composition in a weight ratio of 3,5-di-tert-butyl-4-hydroxy-N,N-dimethylbenzyl amine to carboxylic acid to air, said ratio being 1:1–0.05:0.05–15.

8 Claims, No Drawings

METHOD FOR INHIBITING THE POLYMERIZATION OF STYRENE

The invention relates to the chemical industry, more specifically to the prevention of spontaneous styrene polymerization during a production process.

In the process of isolating a styrene from the products of dehydrogenation of ethylbenzene at the stage of rectification there occurs the spontaneous polymerization of a monomer under high temperature effects, a factor that leads to clogging of facilities with a polymer, which is turn reduces heat transfer, efficiency of the facilities and sometimes causes a halt of production not provided for by the production process. In order to avoid undesirable styrene polymerization, use is made of inhibitors.

Known in the art are methods for inhibiting the polymerization of styrene at high temperatures using a mixture of p-quinone dioxime with hydroquinone (USSR Inventor's Certificate No.257496, 1968) or p-nitrophenol/USSR Inventor's Certificate No.441263, 1972/. However, they display low solubility in aromatic hydrocarbons, which results in clogging transmission pipe lines, the plates and heat-exchangers of columns. The use of p-quinone dioxime suspensions calls for special much power-consuming equipment and, most importantly, said p-quinone dioxime is inflammable and its dust-air mixtures are dangerously explosive.

The most relevant prior art teaches a method of inhibiting the polymerization of styrene with a mixture of 3,5-Di-tert-butyl-4-hydroxy-N,N-dimethylbenzyl amine and aliphatic carboxylic acids/USSR Inventor's Certificate No.819078, 1978/.

The mixture of 3,5-Di-tert-butyl-4-hydroxy-N,N-dimethylbenzyl amine with carboxylic acids /USSR Inventor's Certificate No.819078, 1978/ is substantially an effective inhibitor for polymerizing a styrene at temperatures of up to 120° C. the components thereof exhibiting good solubility in aromatic hydrocarbons, being non-toxic, fire- and explosion proof and inert in respect to the monomer.

Nevertheless, large doses of the inhibitor are big required (0,5–0,22% by weight). At the same time it has been established that a considerable portion of the inhibitor per se is not spent over the residence time in the column, which results in nonproductive loss thereof, consequently there exists the possibility that the efficiency of this specific inhibitor can be improved.

It is an object of the invention to improve efficiency and reduce an amount of the inhibitor consumed.

This object is achieved owing to the fact that the claimed method for inhibiting the polymerization of styrene provides for adding the solution of a mixture of 3,5-Di-tert-butyl-4-hydroxy-N,N-dimethylbenzyl amine and carboxylic acid or an anhydride of said carboxylic acid with a simultaneous supply of air (oxygen) in the weight ratio of 1:1– 0,05:0, 05–15.

Said carboxylic acid used may be represented by, for example, adipic acid, maleic acid, palmic acid, stearic acid, acetic acid, phthalic acid, synthetic fatty acids and as the anhydride - maleic, acetic, phthalic anhydrides.

The ratio of components of the inhibiting composition of 3,5-Di-tert-butyl-4-hydroxy-N,N-dimethylbenzyl amine:acid (acid anhydride) is 1:1–0,05 (prototype). The ratio 1:1–0,2 is the most favourable one and provides a sufficient activity of the inhibitor in a wide range of its concentrations.

An organic solvent may be represented by, for instance, benzene, toluene, xylene, ethylbenzene, styrene, acetophenone, methylphenyl carbinol.

Selection of temperature conditions at the stage of preparing an inhibitor depends on its concentration: more concentrated solutions require elevated temperatures. For instance, a 10% solution of the inhibitor in ethylbenzene can be prepared at 20° C. and in the case of 25–30% it is necessary to heat up to 50° to 60° C.

Oxygen(air) is supplied into a column for separating benzene-toluene fraction and/or a column for separating ethylbenzene as calculated in terms of 0,05–15 weight units per a unit of 3,5-Di-tert-butyl-4-hydroxy-N,N-dimethylbenzil amine, and along with this, the amount of the inhibitor consumed is drastically reduced as is polymer content in the bottom of the columns.

The minimum air flow rate is 0,05 parts by weight per part of 3,5-Di-tert-butyl-4-hydroxy-N,N-dimethylbenzil amine.

The maximum flow rate of 15 wt. parts of the air per part of 3,5-Di-tert-butyl-4-hydroxy-N,N-dimethylbenzyl amine is limited by requirements imposed on the quality of a monomer: an excessive amount of oxygen is bound to increase the content of carbonyl and peroxide compounds in styrene and also by technological causes—in conditions of vacuum rectification, feed of a gaseous substance tends to increase a residual pressure and, consequently, temperature.

The method of testing the efficiency of inhibition is based on the determination of the quantity of a polymer forming in styrene, on initial heating, in the presence of the inhibitor.

For a better understanding of the invention, given below are concrete examples.

Example I (according to the prototype).

A three-necked flask having a dephlegmator, a thermometer and a capillary of the type used for supplying nitrogen is filled with 750 ml of styrene with a basic substance contained in the amount of 99,8% by weight and 2,04 g of a solution containing 0,204 g of 3,5-Di-tert-butyl-4-hydroxy-N,N-dimethylbenzyl amine and 0,102 g of stearic acid in ethylbenzene. The contents of the flask are heated in a nitrogen stream at a temperature of 101°±2° C. and the residual pressure of 200 mm Hg for 3 hours. The pressure is then increased in the flask to atmospheric and a sample was taken for analysis for polymer content in the styrene using the gravimetric method. Polymer content: 1,55% by weight.

Example 2.

A three-necked flask provided with a dephlegmator, a thermometer and a capillary for supplying air is filled with 750 ml of styrene with a basic substance contained in the amount of 99,8% by weight and 2,04 g of a solution containing 0,204 g of 3,5-Di-tert-butyl-4-hydroxy-N,N-dimethylbenzyl amine and 0,102 g of stearic acid in ethylbenzene. The contained matter was heated in air stream fed at a rate of substantially about 40 ml/hr, at 101°±2° C. and a residual pressure of 200 mm Hg for 3 hours, the weight ratio of the components of an inhibitor and air 1:0,5:0,75, by sequentially increasing the pressure in the flask to atmospheric and taking up a sample for analysis for polymer content in the styrene by the gravimetric method. Polymer content: 0,11% by weight.

Example 3.

In the conditions of Example 2 use is made of acetic acid and air is supplied at a rate of substantially about 260 ml/hr, and more importantly, the ratio of the components of an inhibitor and air are 1:0,5:4,9. After 3 hours of initial heating the polymer content is 0,058% by weight.

Example 4.

A three-necked flask equipped with a dephlegmator, a thermometer and a capillary for air supply is filled with 750 ml of styrene with a basic substance contained in the amount of 99,8% by weight and 2,04 g of a solution containing 0,204 g of 3,5-Di-tert-butyl-4-hydroxy-N,N-dimethylbenzil amine and 0,204 g of palmitic acid in ethylbenzene. The contents of the flask are heated in air stream supplied at a rate of substantially about 420 ml/hr, at 101°±2° C. and the residual pressure of 200 mm Hg for 3 hours, and along with this, the weight ratio of the components of an inhibitor and air are 1:1:8. The pressure in the flask is then increased to atmospheric and a sample is taken for analysis for polymer content in the styrene using a nephelometric method. No polymer is present.

Example 5.

A three-necked flask having a dephlegmator, a thermometer and a capillary for air supply is filled with 750 ml of styrene with a basic substance contained in the amount of 99,7% by weight and 2,04 g of a solution containing 0,204 g of 3,5-Di-tert-butyl-4-hydroxy-N,N-dimethylbenzyl amine and 0,204 g of acetic anhydride in the styrene. The contents of the flask are heated in air stream to be supplied at the rate of 800 ml/hr, at 101°±2° C. and the residual pressure of 200 mm Hg for 3 hours, and the weight ratio of the components of the inhibitor and air are 1:1:15. The pressure in the flask is then increased to atmospheric and a sample is taken for analysis for polymer content in the styrene using a nephelometric method. No polymer is present.

Example 6.

According to the run of Example 2, air is supplied at the rate of 1,55 l/hr and the weight ratio of the components of an inhibitor and air are 1:0,5:30. The pressure in the flask is then increased to atmospheric and a sample is taken up for analysis for polymer content in styrene according to the nephelometric method. After 3 hours of initial heating, no polymer in the styrene is found.

Example 7.

In accordance with the procedure of Example 2, air is fed at the rate of 2,6 ml/hr, and the weight ratio of the components of an inhibitor and air is 1:0,5:0,05. The pressure in the flask is then increased to atmospheric and a sample is taken up for analysis for polymer content in styrene by the gravimetric method. After 3 hours of initial heating, the styrene contains 1,45% by weight of polymer.

Example 8.

A three-necked flask having a dephlegmator, a thermometer and a capillary for air supply is filled with 3 750 ml of styrene with a basic substance contained in the amount of 99,8% by weight and 3,4 g of the xylene solution of an inhibitor containing 0,34 g of 3,5-Di-tert-butyl-4-hydroxy-N,N-dimethylbenzyl amine and 0,374 g of stearic acid. Air is supplied at a rate of substantially about 4 ml/hr and, with this, the weight ratio of the components of the inhibitor and air being 1:1, 1:0,044. The contents of the flask are heated at the temperature 101°±2° C. and the residual pressure of 200 mm Hg for 3 hours. The pressure in the flask is then increased to atmospheric and a sample is taken for analysis for polymer content in the styrene by the gravimetric method. After 3 hours of initial heating, the polymer content is 2,63% by weight.

Example 9.

A three-necked flask equipped with a dephlegmator, a thermometer and a capillary for air supply is filled with 750 ml of styrene with a basic substance contained in the amount of 99,8% by weight and 0,34 g of 3,5-Di-tert-butyl-4-hydroxy-N,N-dimethylbenzil amine and 0,017 g of synthetic fatty acids. Oxygen is supplied at a rate of substantially about 26 ml/hr. The weight ratio of the components of an inhibitor and air is 1:0,05:0,3. The contents of the flask are heated at 101°±2° C. and the residual pressure of 200 mm Hg for 3 hours, whereupon the pressure in the flask is increased to atmospheric and a sample is taken for analysis for polymer content in the styrene by the nephelometric method. After 3 hours of initial heating, the polymer content is 0,01% by weight.

The conclusion is that the supply of air (oxygen) considerably improves the efficiency of an inhibiting composition of 3,5-Di-tert-butyl-4-hydroxy-N,N-dimethylbenzil amine—carboxylic acid (carboxylic acid anhydride).

We claim:

1. In a process for the preparation of styrene, a method for preventing the spontaneous polymerization of styrene wherein an inhibiting composition of 3,5-di-tert-butyl-4-hydroxy-N,N-dimethylbenzyl amine and a carboxylic acid, or an anhydride of said carboxylic acid, in an organic solvent, is added to a styrene-containing mixture, the improvement comprising:

a) supplying air simultaneously with the inhibiting composition in a weight ratio of 3,5-di-tert-butyl-4-hydroxy-N,N-dimethylbenzyl amine to carboxylic acid to air, said ratio being 1:1–0.05:0.05–15.

2. The process as claimed in claim 1 wherein the weight ratio of said 3,5-di-tert-butyl-4-hydroxy-N,N-dimethylbenzyl amine to carboxylic acid, or anhydride of said carboxylic acid is 1:1–0.1.

3. The process as claimed in claim 1 wherein said carboxylic acid is selected from the group consisting of adipic acid, maleic acid, palmic acid, stearic acid and synthetic fatty acids.

4. The process as claimed in claim 1 wherein the weight ratio of 3,5-di-tert-butyl-4-hydroxy-N,N-dimethylbenzyl amine to air is 1:0.3–8.

5. The process as claimed in claim 1 wherein the organic solvent is an aromatic solvent selected from the group consisting of benzene, toluene, xylene, ethylbenzene, styrene, acetophenone, and methylphenyl carbinol.

6. The process as claimed in claim 5 further comprising preheating the organic solvent to a temperature of between 20°–60° C.

7. The process as claimed in claim 1 wherein 3,5-di-tert-butyl- 4-hydroxy-N,N-dimethylbenzyl amine is present in an amount of from 100 to 2000 parts by weight per million parts by weight of styrene.

8. The process as claimed in claim 1 wherein 3,5-di-tert-butyl- 4-hydroxy-N,N-dimethylbenzyl amine is present in an amount of from 250 to 850 parts by weight per million parts by weight of styrene.

* * * * *